United States Patent
Burton

(10) Patent No.: US 7,097,799 B1
(45) Date of Patent: Aug. 29, 2006

(54) PROSTHETIC SOCKET AND METHOD OF MAKING THE SAME

(76) Inventor: Russell F. Burton, 3701 S. 70th St., Omaha, NE (US) 68106

( * ) Notice: Subject to any disclaimer, the term of this patent is extended or adjusted under 35 U.S.C. 154(b) by 271 days.

(21) Appl. No.: 10/783,232

(22) Filed: Feb. 23, 2004

(51) Int. Cl.
  *B29C 33/38* (2006.01)
  *B29C 33/40* (2006.01)

(52) U.S. Cl. .................. 264/223; 264/220; 264/222; 264/225; 264/227

(58) Field of Classification Search ............. 264/220, 264/221, 222, 225, 227, 223
See application file for complete search history.

(56) References Cited

U.S. PATENT DOCUMENTS

| | | | |
|---|---|---|---|
| 3,393,407 A | 7/1968 | Kandel | 3/20 |
| 4,314,398 A | 2/1982 | Pettersson | 29/407 |
| 4,822,371 A * | 4/1989 | Jolly et al. | 623/32 |
| 5,376,132 A | 12/1994 | Caspers | 623/36 |
| 5,718,925 A | 2/1998 | Kristinsson et al. | 425/2 |
| 5,980,576 A | 11/1999 | Graf et al. | 623/33 |
| 6,440,345 B1 * | 8/2002 | Hellberg | 264/222 |
| 6,709,617 B1 * | 3/2004 | Wu | 264/222 |

* cited by examiner

*Primary Examiner*—Allan R. Kuhns
(74) *Attorney, Agent, or Firm*—Thomte, Mazour & Niebergall; Shane M. Niebergall

(57) ABSTRACT

A method of forming prosthetic sockets is provided that first creates a negative mold of the patient's residual limb while it is disposed in a positive flexion position. The mold is then removed and shaped to permit the desired range of flexion when the mold is repositioned on the residual limb. A second cast is made of the residual limb that incorporates the mold. A positive model of the residual limb is then formed, from which test or definitive sockets may be formed. The present method further lends itself to the formation of sockets using a cast-in-place methodology while the limb is disposed in a positive flexion position.

17 Claims, 3 Drawing Sheets

PROSTHETIC SOCKET AND METHOD OF MAKING THE SAME

BACKGROUND OF THE INVENTION

1. Field of the Invention

The present invention relates to sockets for below-knee prosthesis and more particularly to a socket that permits maximum necessary flexion while the prosthesis is secured to a residual limb.

2. Description of the Prior Art

Since the Middle Ages, sockets have provided a measure of protection for the residual limb of amputees, as well as a point of attachment for artificial limbs. Crude forerunners to the modern socket were constructed from iron or wood, which provided limited functionality and even less comfort. Advances in biomechanics and the development of materials such as moldable plastics and plastic laminates have dramatically improved the function and comfort of prosthetic sockets.

Although the modern transtibial, or below-knee, prosthesis can be found in a wide array of designs and configurations, the major components are typically the socket, a suspension system, a pylon and a foot system. As the primary point of contact between the residual limb and the prosthesis, the socket protects the residual limb and transmits the forces associated with standing and ambulation. Any relative motion between the residual limb and the socket oftentimes results in less than satisfactory ambulation and an increase in discomfort and fatigue. In order to obtain a precise fit, transtibial sockets are typically made by first creating a cast of the residual limb in a generally extended position. The cast is later filled with plaster or other molding material to create a positive model for a check socket. The prosthetist manually adjusts the check socket to compensate for any pressure points or bony protrusions. A second positive model of the residual limb is formed by filling the check socket with the molding material. The definitive socket is then prepared using the second positive model.

An increasing number of modern transtibial prosthetics are suspended using a suction suspension, such as hypobaric sleeves and silicone liners. Typical socket construction combined with such modern suspension systems oftentimes create a problem in easily or comfortably obtaining a normal range of motion. Most common socket designs provide a lower, flared posterior trim that is hand-fabricated by the prosthetist to allow for knee flexion. However, the flared posterior trim is typically inadequate to provide a normal range of motion due to the evolving shape of the individual's knee when the residual limb moves between full extension and plus ninety degrees flexion. Not only does the interaction between the rigid socket and the shape-changing knee cause discomfort and a limited range of motion, but it also applies pressure on the suspension system during periods of flexion, causing undo wear and tear on the prosthesis.

Accordingly, what is needed is a novel but simple method of making prosthetic sockets that permits maximum necessary flexion.

SUMMARY OF THE INVENTION

The prosthetic socket of the present invention is formed by applying a moldable material to the residual limb and forming a cast or negative mold of the residual limb in a positive flexion position. The moldable casting material is permitted to cure until it becomes generally rigid so it may be easily removed. In one embodiment, the mold is trimmed and modified so that, when the mold is returned to the residual limb, full essential range of motion is permitted in the adjacent joint. The mold may then be incorporated into any standard casting method typically used by the prosthetist to create a second negative cast of the entire residual limb. A positive model can then be created to assist in the preparation of a check socket or the definitive prosthetic socket.

In another embodiment, the socket of the present invention is formed using one of several cast-in-place systems rather than the moldable casting material. In this manner, a check or definitive socket can be produced in a single step of casting the entire residual limb in a positive flexion position. The socket is then trimmed and adjusted by the prosthetist to perfect the fit.

It is therefore one of the principle objects of the present invention to provide a prosthetic socket that comfortably and securely engages the residual limb while providing full essential range of motion to the adjacent joint.

Another object of the present invention is to provide a prosthetic socket that is formed by casting the residual limb in a positive flexion position.

Still another object of the present invention is to provide a prosthesis socket in a single step by casting the residual limb in a positive flexion position using cast-in-place materials.

Yet another object of the present invention is to provide a prosthetic socket that, while simple to fabricate, reduces the pressures typically inflicted on suspension systems during flexion of the adjacent joint.

Yet another object of the present invention is to provide a method of forming prosthetic sockets that is simple and relatively inexpensive to implement while increasing the relative range of motion attainable by amputees.

These and other objects of the present invention will be apparent to those skilled in the art.

DESCRIPTION OF THE PREFERRED EMBODIMENT

Figure 1:
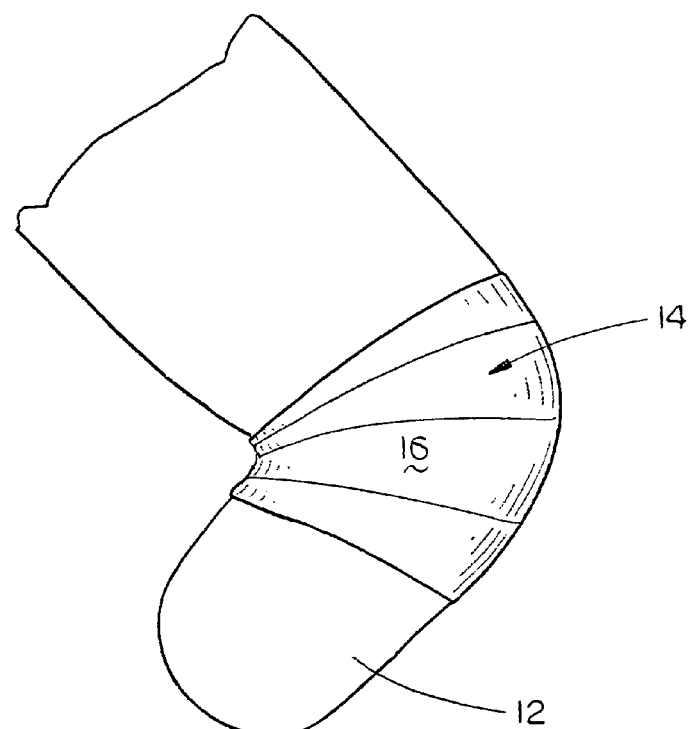
FIG. 1 is a side elevation view of one embodiment of moldable material as it cures or hardens on a residual limb disposed in a positive flexion position.

The prosthetic socket 10 of the present invention is generally depicted in different stages of fabrication and in different embodiments in FIGS. 1–5. The socket 10 is provided for use by an amputee and is received by the residual limb 12 below the knee 14 in the limb. The socket 10 will be described herein as being used for a transtibial prosthetic device for simplicity of description only. The socket 10 of the present invention and the methods of forming the same as described herein will be equally applicable to any prosthetic socket that is utilized on a residual limb adjacent a functional joint.

The socket 10 may be formed for use by an amputee at nearly any post surgical stage where the residual limb 12 remains swollen, serving as a preparatory socket. Thereafter, the socket 10, and methods for forming the same, will serve the amputee well as a definitive socket that provides a natural, full range of motion to the amputee's residual limb 12 and joint 14.

In a preferred embodiment, the socket 10 is formed by first creating a negative mold 18 of the residual limb 12 and joint area 14 using a moldable material 16. Several different types of moldable materials 16 will suffice in the formation of the negative mold 18 of the residual limb 12 and joint 14, including various water-activated orthopedic plaster wraps, or other resin impregnated tapes or socks made from various fabrics, fiberglass or lofted glass yarn. It is also contemplated however that the negative mold 18 of the residual limb 12 and joint 14 could be formed using a moldable material such as alginate, which is prepared by mixing the alginate powder with water to produce the gelatinous substance in which the residual limb 12 and the joint 14 are immersed to produce a mirror image of the residual limb 12 and the joint 14. Regardless of the moldable material utilized by the prosthetist, the residual limb 12 and the joint 14 will be at least partially enveloped by the moldable material 16 and then placed in a positive flexion position. It will be understood that when the residual limb 12 is fully extended that the residual limb 14 is in a position of zero flexion. Plus ninety degree flexion positions will be considered to be those positions where the joint 14 is bent so that the residual limb 12 is disposed at an angle greater than ninety degrees from full extension or zero flexion. Although it is preferred that the moldable material 16 be allowed to start hardening or curing while the residual limb 12 is disposed in a position of maximum flexion, such a point will vary from patient to patient and will depend upon the structural nature of the joint 14 and the physical condition of the patient. However, it is believed that the "maximum necessary flexion" will be attained at or beyond ninety degrees flexion when fabricating the mold 18 and, ultimately, the socket 10.

Figure 2:
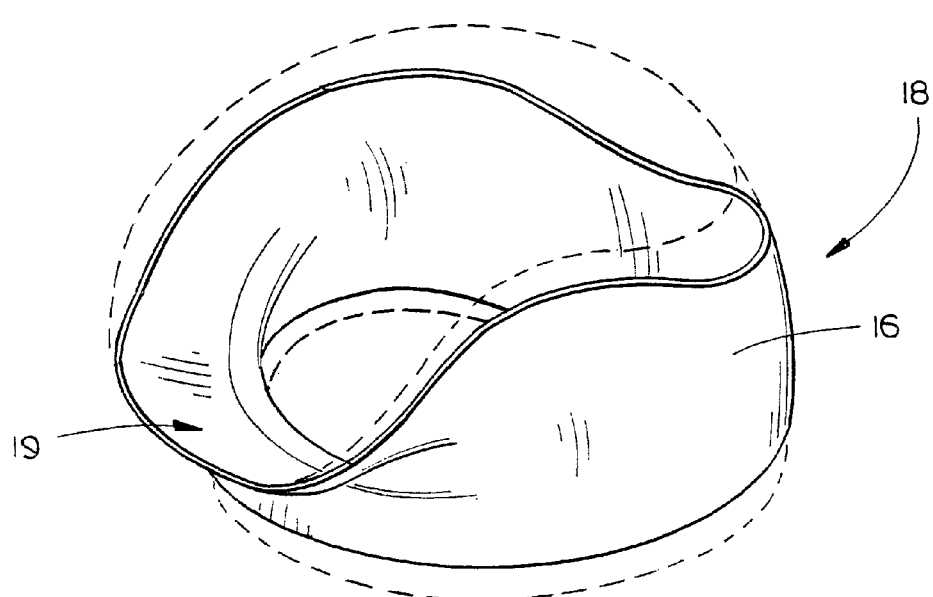
FIG. 2 is a perspective view of one embodiment of a negative mold of a portion of a residual limb that was formed in a positive flexion position.
Figure 4:
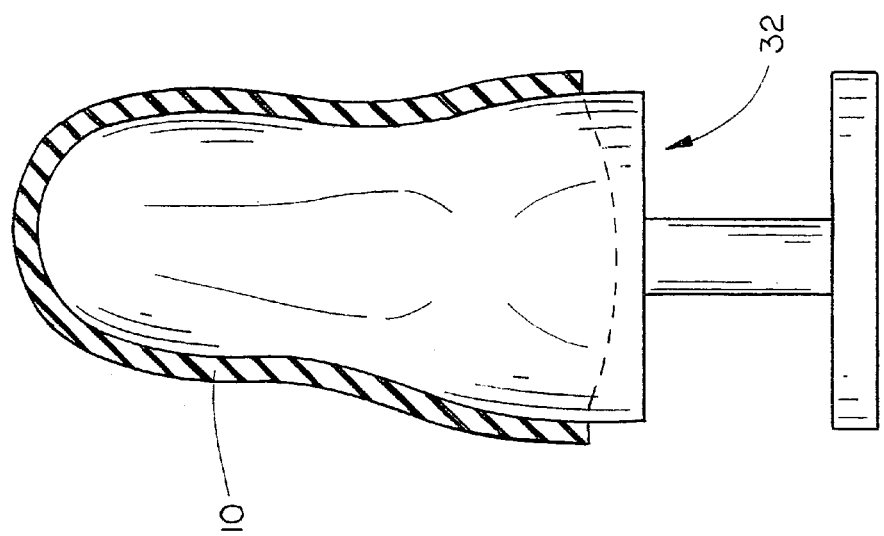
FIG. 4 is a cut-away side elevation view of one embodiment of the socket of the present invention as it may be prepared on a positive model of a residual limb in accordance with the methods of the present invention.
Figure 3:
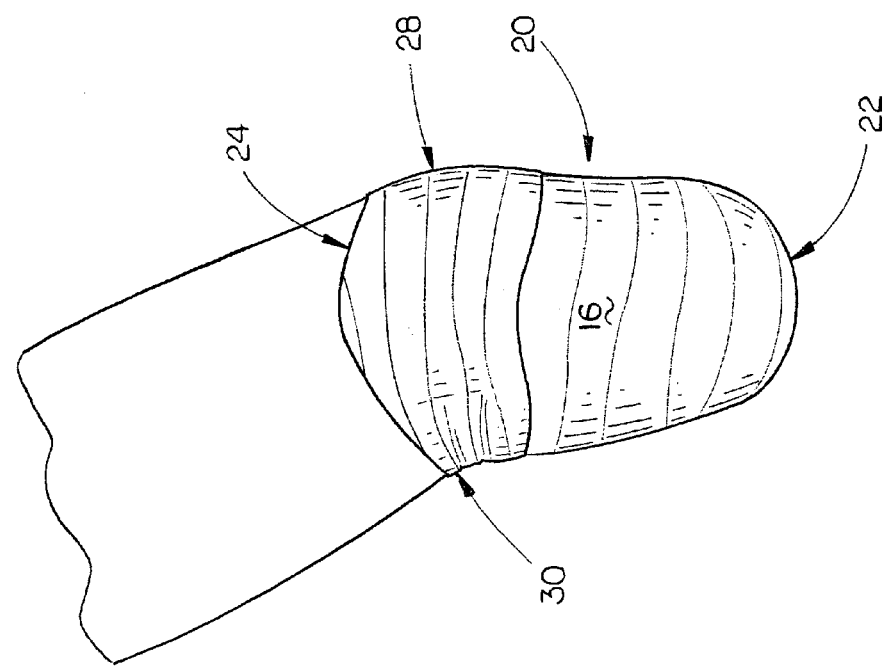
FIG. 3 is a side elevation view of one embodiment of a full negative casting of a residual limb using the methods of the present invention.
Figure 5:
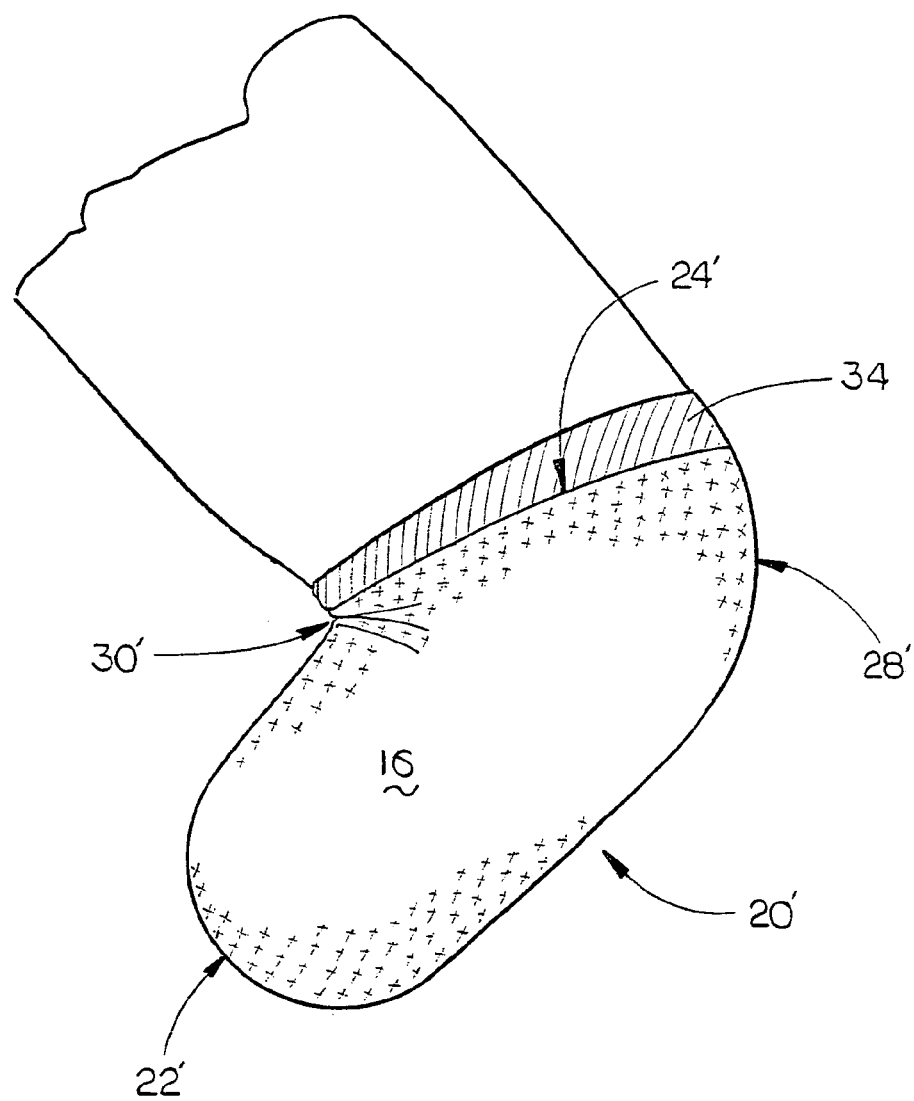
FIG. 5 is a side elevation of another embodiment of a full negative casting of a residual limb in a positive flexion position using cast-in-place materials.

Once the moldable material 16 has at least partially cured or hardened, a negative mold 18 is formed. The mold 18 is removed from the residual limb 12 and the joint 14. In one preferred embodiment, the mold 18 covers only a portion of the residual limb 12 adjacent the joint 14 and a portion of the joint 14 itself. However, it is contemplated that the mold 18 could be initially cast to cover substantially all of the residual limb 12 and the joint 14. Regardless of its size, the mold 18 will naturally be shaped to have a flared posterior portion 19 and may be further shaped and otherwise trimmed (as depicted in FIG. 2) so that when it is returned to the residual limb 12 and the joint 14, full essential (or desired) range of motion is permissible within the joint 14. In this manner, the prosthetist will be assured that the definitive socket 10 will allow for a natural, full range of motion during ambulation or various positions of flexion, such as when the individual is seated. The degree of cutting and shaping required will vary from instance to instance and it is also contemplated that no shaping or cutting may be required on some occasions.

Where only a portion of the residual limb 12 and the joint 14 are covered by the mold 18 a full mold or cast 20 will need to be formed. First, the prosthetist returns the mold 18 to the residual limb 12 and the joint 14. A moldable material 16 is then applied to the residual limb 12 and the mold 18 so that the mold 18 becomes incorporated with the resulting cast 20. This step may be performed while the patient's residual limb 12 is in virtually any position, due to the fact that the moldable material 16 will mostly be applied to the distal end of the residual limb 12. Where the initial mold 18 covers substantially all of the residual limb 12, this step will likely be unnecessary as the mold 18 and the full cast 20 would be nearly identical to one another.

Once fully cured or hardened, the cast 20 will greatly resemble the preparatory or definitive socket 10 and in some applications may serve as either, having a lower closed end 22, an upper open end portion 24 and an inner chamber, which closely mirrors the contours and dimensions of the residual limb 12 and at least a portion of the joint 14. The upper open end portion 24 will preferably have a forward end portion 28 having a shape conforming to the forward portion of the joint 14, such as the patella and patellar tendon when the joint 14 is the patient's knee. Due to the positive flexion position of the residual limb 12 during casting, the rearward end portion 30 of the upper open end portion 24 will be automatically shaped and sized to accommodate the changing shape of the joint 14 and adjacent structural details of the limb throughout a normal range of ambulation for the patient.

A positive model 32 of the residual limb 12 and at least a portion of the joint 14 can then be fabricated by applying one of various materials, such as plaster, various compositions of rubber, plastic, foam and the like. Rectification of the positive model 32 should reflect all proximal trim and related volume requirements that will allow normal flexion while the socket 10 is securely retained by a socket suspension system. Once the positive model 32 is complete the socket 10 can be fabricated therefrom using various materials such as plastic polymer laminates (thermosets), or other traditional materials such as wood, steel and leather as well as more advanced materials such as titanium, carbon fiber and various plastics. Thermosets using a reinforcement textile such as fiberglass, nylon, carbon, or Kevlar, and a resin such as acrylic, epoxy and polyester, may be preferred due to their strength to weight ratio as well as the ease and relative low cost in working with such materials.

It is contemplated that a "one-step" process could be used with the methods of making the socket 10 taught herein. Such a one-step method of fabrication will substitute a cast-in-place material such as a resin impregnated flexible sock comprised of a material such as carbon fiber or lofted glass yarn for the moldable material 16. One cast-in-place system of this general nature, which could be utilized with the present method is the Ossur USA ICEX system. Regardless of the specific materials selected, the materials should be applied to the residual limb 12 and the joint 14 such that the material may be allowed to cure or harden substantially while the residual limb 12 is in its positive flexion position. Special care should be used so that the resulting cast 20' can be removed from the residual limb 12 once the material has begun to cure or harden. Accordingly, it may be desirable to apply a thin casting sock 34 to the residual limb 12 and the joint 14 prior to the application of the moldable material. Once the cast 20 has fully cured or hardened, final adjustments through shaping and trimming can be performed in order to provide the appropriate measure of support, control, and alignment.

The socket 10 can include a liner such as OWW Alpha Liners, TEC Liners and the like, worn by the patient in order to cushion the forces on the residual limb 12. It is contemplated that the socket 10 can be easily adapted for engagement with the residual limb by a variety of suspension mechanisms, such as belts, wedges, straps, suction or a combination thereof. The design of the socket 10, more particularly the custom formed rearward end portion 30 of the upper open end 24 will eliminate pressures typically induced on suspension systems, such as silicone suction sleeves during periods of joint flexion.

It is contemplated that the present method of forming the socket 10 will lend itself well to the application of CAD-CAM (computer aided design, computer aided manufacture) technology. It will be understood that, using the present method, precise measurements of the residual limb 12 and the joint 14 will be obtained through optical sensors or other appropriate means and input into the CAD software for the creation of a three dimensional negative mold or positive model of the residual limb 12 in a positive flexion position. The resulting computer generated positive model of the residual limb 12 will provide the CAM devices to fabricate an accurate test socket. Adjustments can be made to the positive model using the CAD software in order to derive the definitive socket 10.

In the drawings and in the specification, there have been set forth preferred embodiments of the invention and although specific items are employed, these are used in a generic and descriptive sense only and not for purposes of limitation. Changes in the form and proportion of parts, as well as a substitution of equivalents, are contemplated as circumstances may suggest or render expedient without departing from the spirit or scope of the invention as further defined in the following claims.

Thus it can be seen that the invention accomplishes at least all of its stated objectives.

I claim:

1. A method of providing a prosthetic socket for a residual limb that extends distally from a joint, comprising the steps of:
   positioning the residual limb in an approximately ninety degree or greater flexion position;
   applying moldable means over at least a portion of the residual limb and joint;
   permitting said moldable means to cure and form a negative mold of at least a portion of the residual limb and joint; and
   removing said mold from the residual limb and joint.

2. The method of claim 1 further comprising the step of shaping said mold so that a desired range of motion in the joint is permitted when said mold is repositioned on the residual limb.

3. The method of claim 2 further comprising the step of forming a positive model of the residual limb using said mold.

4. The method of claim 3 further comprising the step of constructing the socket over the positive model of the residual limb.

5. The method of claim 4 further comprising the step of reducing and building up the positive model of the residual limb prior to the step of constructing the socket.

6. The method of claim 2 further comprising the step of repositioning said mold onto the residual limb after the step of shaping said mold.

7. The method of claim 6 further comprising the step of making a cast of the residual limb that incorporates said mold.

8. The method of claim 7 further comprising the step of forming a positive model of the residual limb using said cast.

9. The method of claim 8 further comprising the step of constructing the socket over the positive model of the residual limb.

10. The method of claim 9 further comprising the step of reducing and building up the positive model of the residual limb prior to the step of constructing the socket.

11. The method of claim 1 further comprising the step of fitting a liner onto the residual limb and joint prior to the step of applying said moldable means over the residual limb and joint.

12. The method of claim 11 wherein said liner is comprised of silicone.

13. The method of claim 11 wherein said moldable means is comprised of a resin-impregnated flexible sock.

14. The method of claim 13 wherein said sock is comprised of carbon fibers.

15. The method of claim 13 wherein said sock is comprised of a lofted glass yarn.

16. The method of claim 13 further comprising the step of adapting said mold to be coupled to a prosthetic appendage.

17. The method of claim 16 further comprising the step of adapting said mold to be operatively coupled to a suspension system.

* * * * *